(12) United States Patent
Douglas Ivan (10) Patent No.: US 9,731,080 B2
(45) Date of Patent: Aug. 15, 2017

(54) INJECTION DEVICE

(75) Inventor: Jennings Douglas Ivan, Royston (GB)

(73) Assignee: Cilag gmBh International, Zug (CH)

( * ) Notice: Subject to any disclaimer, the term of this patent is extended or adjusted under 35 U.S.C. 154(b) by 1034 days.

(21) Appl. No.: 11/910,536

(22) PCT Filed: Apr. 3, 2006

(86) PCT No.: PCT/GB2006/001018
§ 371 (c)(1),
(2), (4) Date: Nov. 11, 2008

(87) PCT Pub. No.: WO2006/106291
PCT Pub. Date: Oct. 12, 2006

(65) Prior Publication Data
US 2009/0234297 A1   Sep. 17, 2009

(30) Foreign Application Priority Data

Apr. 6, 2005   (GB) .................... 0507001.6

(51) Int. Cl.
*A61M 5/32* (2006.01)
*A61M 5/20* (2006.01)

(52) U.S. Cl.
CPC ........ *A61M 5/3243* (2013.01); *A61M 5/2033* (2013.01); *A61M 5/3202* (2013.01); *A61M 5/3204* (2013.01); *A61M 2005/208* (2013.01); *A61M 2005/2086* (2013.01)

(58) Field of Classification Search
CPC .......... A61M 2005/208; A61M 5/3243; A61M 5/2033; A61M 5/3202; A61M 5/32; A61M 2005/3215; A61M 5/3275; A61M 5/3276

USPC .......... 604/195, 110, 181, 187, 192
See application file for complete search history.

(56) References Cited

U.S. PATENT DOCUMENTS

| 1,845,036 | A | 2/1932 | Busher |
| 2,019,382 | A | 10/1935 | Aronson |
| 2,147,616 | A | 2/1939 | Chaput |
| 2,295,849 | A | 9/1942 | Kayden |
| 2,531,267 | A | 11/1950 | Harisch |

(Continued)

FOREIGN PATENT DOCUMENTS

| CA | 2445511 A1 | 11/2002 |
| CH | 518102 A | 1/1972 |

(Continued)

OTHER PUBLICATIONS

International Search Report dated Sep. 5, 2005; International Application No. PCT/GB2005/002117.

(Continued)

*Primary Examiner* — Kevin C Sirmons
*Assistant Examiner* — Deanna K Hall (57) ABSTRACT

An injection device (110) comprises a housing (112) having a syringe (114) with a discharge nozzle (118). The syringe is movable between a retracted position in which the discharge nozzle is contained within the housing and an extended position in which the discharge nozzle extends from the housing. There is syringe cap (180) for enclosing the discharge nozzle. The syringe cap is removable from the syringe by rotation to the syringes. A syringe carrier (150) in the housing is adapted to restrain rotation of the syringe relative to the housing as the cap is removed.

6 Claims, 5 Drawing Sheets

(56) References Cited

U.S. PATENT DOCUMENTS

| | | |
|---|---|---|
| 2,764,977 A | 10/1956 | Ferguson |
| 2,828,742 A | 4/1958 | Ashkenaz |
| 2,854,975 A | 10/1958 | Cohen |
| 3,076,455 A | 2/1963 | McConnaughey et al. |
| 3,131,692 A | 5/1964 | Love |
| 3,320,955 A | 5/1967 | Sarnoff |
| 3,329,146 A | 7/1967 | Waldman |
| 3,543,603 A | 12/1970 | Gley |
| 3,656,472 A | 4/1972 | Moura |
| 3,702,608 A | 11/1972 | Tibbs |
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 3,976,069 A | 8/1976 | Ong |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,222,380 A | 9/1980 | Terayama |
| 4,231,368 A | 11/1980 | Becker |
| 4,236,516 A | 12/1980 | Nilson |
| 4,237,882 A * | 12/1980 | Wickham .............. A61M 5/347 604/192 |
| 4,299,238 A | 11/1981 | Baidwan et al. |
| 4,333,459 A | 6/1982 | Becker |
| 4,378,015 A | 3/1983 | Wardlaw |
| 4,394,863 A | 7/1983 | Bartner |
| 4,403,989 A | 9/1983 | Christensen et al. |
| 4,407,283 A | 10/1983 | Reynolds |
| 4,425,120 A * | 1/1984 | Sampson et al. ............ 604/198 |
| 4,430,082 A | 2/1984 | Schwabacher |
| 4,521,237 A | 6/1985 | Logothetis |
| 4,561,856 A | 12/1985 | Cochran et al. |
| 4,627,835 A | 12/1986 | Fenton, Jr. |
| 4,636,201 A | 1/1987 | Ambrose et al. |
| 4,639,250 A | 1/1987 | Rycroft |
| 4,642,099 A | 2/1987 | Phillips et al. |
| 4,676,530 A | 6/1987 | Nordgren et al. |
| 4,717,383 A | 1/1988 | Phillips et al. |
| 4,744,786 A | 5/1988 | Hooven et al. |
| 4,787,891 A | 11/1988 | Levin et al. |
| 4,874,383 A * | 10/1989 | McNaughton ................ 604/198 |
| 4,874,384 A | 10/1989 | Nunez |
| 4,929,232 A | 5/1990 | Sweeney et al. |
| 4,969,870 A | 11/1990 | Kramer et al. |
| 4,988,339 A | 1/1991 | Vadher |
| 4,994,034 A | 2/1991 | Botich et al. |
| 5,009,646 A | 4/1991 | Sudo et al. |
| 5,026,349 A | 6/1991 | Schmitz et al. |
| 5,057,079 A | 10/1991 | Tiemann et al. |
| 5,092,842 A | 3/1992 | Bechtold et al. |
| 5,098,400 A | 3/1992 | Crouse et al. |
| 5,112,119 A | 5/1992 | Cooke et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,147,325 A | 9/1992 | Mitchell et al. |
| 5,156,599 A | 10/1992 | Ranford et al. |
| 5,176,643 A | 1/1993 | Kramer et al. |
| 5,190,526 A | 3/1993 | Murray et al. |
| 5,242,416 A | 9/1993 | Hutson |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,312,364 A | 5/1994 | Jacobs |
| 5,330,081 A | 7/1994 | Davenport |
| 5,330,430 A | 7/1994 | Sullivan |
| 5,356,395 A | 10/1994 | Chen |
| 5,358,489 A | 10/1994 | Wyrick |
| 5,364,369 A | 11/1994 | Reynolds |
| 5,368,577 A | 11/1994 | Teoh et al. |
| 5,372,586 A | 12/1994 | Haber et al. |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,503,627 A | 4/1996 | McKinnon et al. |
| 5,514,097 A | 5/1996 | Knauer |
| 5,520,653 A | 5/1996 | Reilly et al. |
| 5,540,660 A | 7/1996 | Jenson et al. |
| 5,540,666 A | 7/1996 | Barta et al. |
| 5,540,709 A | 7/1996 | Ramel et al. |
| 5,567,160 A | 10/1996 | Massino |
| 5,569,191 A | 10/1996 | Meyer |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,607,395 A | 3/1997 | Ragsdale et al. |
| 5,609,577 A | 3/1997 | Haber et al. |
| 5,609,584 A | 3/1997 | Gettig et al. |
| 5,611,785 A | 3/1997 | Mito et al. |
| 5,637,094 A | 6/1997 | Stewart, Jr. et al. |
| 5,645,536 A | 7/1997 | Whisson |
| 5,647,845 A | 7/1997 | Haber et al. |
| 5,649,912 A | 7/1997 | Peterson |
| 5,658,259 A | 8/1997 | Pearson et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A | 1/1998 | Olive et al. |
| 5,713,866 A | 2/1998 | Wilmot |
| 5,748,316 A | 5/1998 | Wakabayashi et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,827,262 A | 10/1998 | Neftel et al. |
| 5,843,036 A | 12/1998 | Olive et al. |
| 5,855,839 A | 1/1999 | Brunel |
| 5,865,795 A | 2/1999 | Schiff et al. |
| 5,865,804 A | 2/1999 | Bachynsky |
| 5,868,711 A | 2/1999 | Kramer et al. |
| 5,879,327 A | 3/1999 | Moreau DeFarges et al. |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |
| 5,997,513 A | 12/1999 | Smith et al. |
| 6,007,515 A | 12/1999 | Epstein et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross |
| 6,123,684 A | 9/2000 | Deboer et al. |
| 6,139,534 A | 10/2000 | Niedospial, Jr. et al. |
| 6,159,161 A | 12/2000 | Hodosh |
| 6,159,181 A | 12/2000 | Crossman et al. |
| 6,159,184 A * | 12/2000 | Perez .................. A61M 5/3271 604/192 |
| 6,162,199 A | 12/2000 | Geringer |

(56) References Cited

U.S. PATENT DOCUMENTS

| | | | |
|---|---|---|---|
| 6,171,276 B1 | 1/2001 | Lippe et al. | |
| 6,179,812 B1 | 1/2001 | Botich et al. | |
| 6,186,980 B1* | 2/2001 | Brunel | A61M 5/3202 |
| | | | 604/110 |
| 6,190,363 B1 | 2/2001 | Gabbard et al. | |
| 6,193,696 B1 | 2/2001 | Jansen et al. | |
| 6,203,530 B1 | 3/2001 | Stewart, Sr. | |
| 6,209,738 B1 | 4/2001 | Jansen et al. | |
| 6,221,044 B1 | 4/2001 | Grecco | |
| 6,228,055 B1 | 5/2001 | Foerster et al. | |
| 6,258,068 B1 | 7/2001 | Kirchhofer et al. | |
| 6,270,479 B1 | 8/2001 | Bergens et al. | |
| 6,280,421 B1 | 8/2001 | Kirchhofer et al. | |
| 6,290,683 B1 | 9/2001 | Erez et al. | |
| 6,293,925 B1 | 9/2001 | Safabash et al. | |
| RE37,439 E | 11/2001 | Firth et al. | |
| 6,317,939 B1 | 11/2001 | Malin | |
| 6,330,960 B1 | 12/2001 | Faughey et al. | |
| 6,332,875 B2 | 12/2001 | Inkpen et al. | |
| 6,371,939 B2 | 4/2002 | Bergens et al. | |
| 6,371,959 B1 | 4/2002 | Trice | |
| 6,387,078 B1 | 5/2002 | Gillespie, III | |
| 6,391,003 B1 | 5/2002 | Lesch, Jr. | |
| 6,419,658 B1* | 7/2002 | Restelli et al. | 604/110 |
| 6,428,528 B2 | 8/2002 | Sadowski et al. | |
| 6,447,480 B1 | 9/2002 | Brunel | |
| 6,454,743 B1 | 9/2002 | Weber | |
| 6,454,746 B1 | 9/2002 | Bydion et al. | |
| 6,461,333 B1 | 10/2002 | Frezza | |
| 6,491,667 B1 | 12/2002 | Keane et al. | |
| 6,517,517 B1 | 2/2003 | Farrugia et al. | |
| 6,537,252 B1 | 3/2003 | Hansen | |
| 6,544,234 B1 | 4/2003 | Gabriel | |
| 6,565,540 B1 | 5/2003 | Perouse et al. | |
| 6,565,553 B2 | 5/2003 | Sadowski et al. | |
| 6,569,115 B1 | 5/2003 | Barker et al. | |
| 6,569,123 B2 | 5/2003 | Alchas et al. | |
| 6,569,124 B1 | 5/2003 | Perouse | |
| 6,572,581 B1 | 6/2003 | Landau | |
| 6,575,939 B1* | 6/2003 | Brunel | 604/187 |
| 6,585,702 B1 | 7/2003 | Brunel | |
| 6,589,210 B1 | 7/2003 | Rolfe | |
| 6,595,957 B1 | 7/2003 | Griffiths et al. | |
| 6,595,962 B1 | 7/2003 | Perthu | |
| 6,599,272 B1 | 7/2003 | Hjertman et al. | |
| 6,607,508 B2 | 8/2003 | Knauer | |
| 6,607,510 B2 | 8/2003 | Landau | |
| 6,613,022 B1 | 9/2003 | Doyle | |
| 6,620,137 B2 | 9/2003 | Kirchhofer et al. | |
| 6,638,256 B2 | 10/2003 | Jansen et al. | |
| 6,641,554 B2 | 11/2003 | Landau | |
| 6,641,560 B1 | 11/2003 | Bechtold et al. | |
| 6,641,565 B1 | 11/2003 | Lavi et al. | |
| 6,645,170 B2 | 11/2003 | Landau | |
| 6,645,181 B1 | 11/2003 | Lavi et al. | |
| 6,648,835 B1 | 11/2003 | Shemesh | |
| 6,648,850 B2 | 11/2003 | Landau | |
| 6,656,163 B1 | 12/2003 | Marshall et al. | |
| 6,673,049 B2 | 1/2004 | Hommann et al. | |
| 6,676,630 B2 | 1/2004 | Landau et al. | |
| 6,689,093 B2 | 2/2004 | Landau et al. | |
| 6,692,469 B1 | 2/2004 | Weekes et al. | |
| 6,699,220 B2 | 3/2004 | Rolfe | |
| 6,740,062 B2 | 5/2004 | Hjertman | |
| 6,743,199 B2 | 6/2004 | Shue et al. | |
| 6,743,203 B1 | 6/2004 | Pickhard et al. | |
| 6,746,429 B2 | 6/2004 | Sadowski et al. | |
| 6,746,438 B1 | 6/2004 | Arnissolle | |
| 6,767,336 B1 | 7/2004 | Kaplan | |
| 6,770,056 B2 | 8/2004 | Price et al. | |
| 6,776,777 B2 | 8/2004 | Barelle | |
| 6,783,509 B1 | 8/2004 | Landau et al. | |
| 6,793,161 B2 | 9/2004 | Fujita et al. | |
| 6,796,967 B2 | 9/2004 | Jensen | |
| 6,811,548 B2 | 11/2004 | Jeffrey | |
| 6,817,987 B2 | 11/2004 | Vetter et al. | |
| 6,846,303 B2 | 1/2005 | Eakins et al. | |
| 6,875,205 B2 | 4/2005 | Leinsing | |
| 6,890,319 B1 | 5/2005 | Crocker | |
| 6,899,698 B2 | 5/2005 | Sams | |
| 6,902,543 B1 | 6/2005 | Cherif-Cheikh et al. | |
| 6,932,793 B1 | 8/2005 | Marshall et al. | |
| 6,939,319 B1 | 9/2005 | Anstead et al. | |
| 6,939,330 B1 | 9/2005 | McConnell-Montalvo et al. | |
| 6,979,316 B1 | 12/2005 | Rubin et al. | |
| 7,066,907 B2 | 6/2006 | Crossman et al. | |
| 7,097,071 B2 | 8/2006 | Anderson et al. | |
| 7,097,634 B2 | 8/2006 | Gilbert | |
| 7,118,553 B2 | 10/2006 | Scherer | |
| 7,156,823 B2 | 1/2007 | Landau et al. | |
| 7,160,913 B2 | 1/2007 | Schneider | |
| 7,294,122 B2 | 11/2007 | Kubo et al. | |
| 7,354,427 B2 | 4/2008 | Fangrow | |
| RE40,428 E | 7/2008 | Keane et al. | |
| 7,442,185 B2 | 10/2008 | Amark et al. | |
| 7,470,258 B2 | 12/2008 | Barker et al. | |
| 7,507,227 B2 | 3/2009 | Fangrow | |
| 7,510,547 B2 | 3/2009 | Fangrow | |
| 7,510,548 B2 | 3/2009 | Fangrow | |
| 7,513,895 B2 | 4/2009 | Fangrow | |
| 7,534,238 B2 | 5/2009 | Fangrow | |
| 7,547,300 B2 | 6/2009 | Fangrow | |
| 7,569,043 B2 | 8/2009 | Fangrow | |
| 7,618,396 B2 | 11/2009 | Slate et al. | |
| 7,635,356 B2 | 12/2009 | Stamp | |
| 7,645,271 B2 | 1/2010 | Fangrow | |
| 7,654,995 B2 | 2/2010 | Warren et al. | |
| 7,658,733 B2 | 2/2010 | Fangrow | |
| 7,678,333 B2 | 3/2010 | Reynolds et al. | |
| 7,682,345 B2 | 3/2010 | Savage | |
| 7,717,879 B2 | 5/2010 | Mansouri | |
| 7,744,561 B2 | 6/2010 | Stamp | |
| 7,759,654 B2 | 7/2010 | Yan et al. | |
| 7,794,434 B2 | 9/2010 | Mounce et al. | |
| 7,799,009 B2 | 9/2010 | Niedospial, Jr. et al. | |
| 7,811,262 B2 | 10/2010 | Moberg et al. | |
| 7,828,764 B2 | 11/2010 | Moberg et al. | |
| 7,871,397 B2 | 1/2011 | Schraga | |
| 7,879,010 B2 | 2/2011 | Hunn et al. | |
| 7,883,499 B2 | 2/2011 | Fangrow | |
| 7,959,715 B2 | 6/2011 | Kavazov et al. | |
| 7,972,321 B2 | 7/2011 | Fangrow | |
| 7,976,499 B2 | 7/2011 | Grunhut et al. | |
| 8,100,154 B2 | 1/2012 | Reynolds et al. | |
| 8,177,768 B2 | 5/2012 | Leinsing | |
| 8,277,414 B2 | 10/2012 | Barrow-Williams et al. | |
| 8,313,463 B2 | 11/2012 | Barrow-Williams et al. | |
| 8,409,138 B2 | 4/2013 | James et al. | |
| 8,409,141 B2 | 4/2013 | Johansen et al. | |
| 8,491,530 B2 | 7/2013 | Maritan | |
| 8,696,628 B2 | 4/2014 | Grunhut | |
| 8,932,264 B2 | 1/2015 | DeSalvo | |
| 9,314,574 B2 | 4/2016 | Roberts et al. | |
| 2001/0005781 A1 | 6/2001 | Bergens et al. | |
| 2001/0021828 A1 | 9/2001 | Fischer et al. | |
| 2001/0037087 A1 | 11/2001 | Knauer | |
| 2001/0037089 A1 | 11/2001 | Domici, Jr. | |
| 2001/0049496 A1 | 12/2001 | Kirchhofer et al. | |
| 2001/0051789 A1 | 12/2001 | Parsons | |
| 2002/0032412 A1 | 3/2002 | Riemelmoser | |
| 2002/0072709 A1 | 6/2002 | Sadowski et al. | |
| 2002/0095120 A1 | 7/2002 | Larsen et al. | |
| 2002/0151839 A1 | 10/2002 | Landau | |
| 2002/0161334 A1 | 10/2002 | Castellano et al. | |
| 2002/0165500 A1* | 11/2002 | Bechtold | A61M 5/2033 |
| | | | 604/209 |
| 2002/0173752 A1 | 11/2002 | Polzin | |
| 2002/0183690 A1 | 12/2002 | Arnisolle | |
| 2003/0036679 A1 | 2/2003 | Kortenbach | |
| 2003/0036725 A1 | 2/2003 | Lavi et al. | |
| 2003/0050609 A1 | 3/2003 | Sams | |
| 2003/0060773 A1 | 3/2003 | Nguyen | |
| 2003/0065286 A1 | 4/2003 | Landau | |
| 2003/0078546 A1 | 4/2003 | Jensen | |

(56) References Cited

U.S. PATENT DOCUMENTS

| | | |
|---|---|---|
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sahpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La Serna et al. |
| 2003/0236502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0094396 A1 | 5/2004 | Lee et al. |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0113747 A1 | 5/2005 | Moir |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178630 A1 | 8/2006 | Bostrom et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1 | 8/2006 | Reynolds |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0066939 A1 | 3/2007 | Krulevitch et al. |
| 2007/0078382 A1 | 4/2007 | Hommann et al. |
| 2007/0118094 A1 | 5/2007 | Bingham et al. |
| 2007/0142787 A1 | 6/2007 | Scherer |
| 2007/0156091 A1 | 7/2007 | Fathallah et al. |
| 2007/0156112 A1 | 7/2007 | Walsh |
| 2007/0208296 A1 | 9/2007 | Paproski et al. |
| 2008/0033395 A1 | 2/2008 | Alchas |
| 2008/0172024 A1 | 7/2008 | Yow |
| 2008/0213590 A1 | 9/2008 | Greiner et al. |
| 2008/0269680 A1 | 10/2008 | Ibranyan et al. |
| 2008/0306443 A1 | 12/2008 | Neer et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Timothy Donald et al. |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2010/0063444 A1 | 3/2010 | Wikner |
| 2011/0092954 A1 | 4/2011 | Jennings |
| 2011/0098647 A1 | 4/2011 | Jennings |
| 2011/0098655 A1 | 4/2011 | Jennings et al. |
| 2011/0130743 A1 | 6/2011 | Jennings et al. |
| 2011/0282278 A1 | 11/2011 | Stamp et al. |
| 2012/0232491 A1 | 9/2012 | Jennings |
| 2012/0323177 A1 | 12/2012 | Adams et al. |
| 2013/0096512 A1 | 4/2013 | Ekman et al. |
| 2013/0267898 A1 | 10/2013 | Hourmand et al. |
| 2013/0317446 A1 | 11/2013 | Hourmand et al. |
| 2013/0331794 A1 | 12/2013 | Ekman et al. |
| 2013/0338601 A1 | 12/2013 | Cowe |
| 2013/0345643 A1 | 12/2013 | Hourmand et al. |
| 2014/0257193 A1 | 9/2014 | Bostr m et al. |

FOREIGN PATENT DOCUMENTS

| | | |
|---|---|---|
| CN | 2059579 U | 7/1990 |
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 1/1997 |
| DE | 19603707 A1 | 8/1997 |
| DE | 69506521 T2 | 6/1999 |
| DE | 10137962 A1 | 2/2003 |

(56) References Cited

FOREIGN PATENT DOCUMENTS

| | | |
|---|---|---|
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0338806 A2 | 10/1989 |
| EP | 0515473 B1 | 12/1992 |
| EP | 0518416 A1 | 12/1992 |
| EP | 0331452 A2 | 8/1993 |
| EP | 0585626 A1 | 3/1994 |
| EP | 0389938 B1 | 5/1994 |
| EP | 0516473 B1 | 2/1996 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1755710 A1 | 2/2007 |
| EP | 1586341 B1 | 1/2008 |
| EP | 1932558 A1 * | 6/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 2468330 A1 | 6/2012 |
| EP | 2340863 B1 | 11/2013 |
| EP | 2620174 B1 | 5/2014 |
| EP | 2675509 B1 | 4/2015 |
| EP | 2705861 B1 | 4/2015 |
| EP | 2414003 B1 | 5/2015 |
| EP | 2464401 B1 | 5/2015 |
| EP | 2493531 B1 | 7/2015 |
| EP | 2705862 B1 | 7/2015 |
| EP | 2588173 B1 | 10/2015 |
| EP | 2470241 B1 | 11/2015 |
| EP | 2768556 B1 | 12/2015 |
| EP | 2355872 B1 | 1/2016 |
| EP | 2720738 B1 | 1/2016 |
| EP | 1412000 B1 | 2/2016 |
| EP | 2671606 B1 | 3/2016 |
| EP | 2760507 B1 | 4/2016 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 | 5/1920 |
| GB | 0412054 | 6/1934 |
| GB | 728248 | 4/1955 |
| GB | 909898 | 11/1962 |
| GB | 1263355 | 2/1972 |
| GB | 1311937 A | 3/1973 |
| GB | 1514725 | 6/1978 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| GB | 2515041 B | 12/2014 |
| JP | 59-115053 A | 7/1984 |
| JP | 2-185261 A | 7/1990 |
| JP | 2-502971 T | 9/1990 |
| JP | H 02-299660 A | 12/1990 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | H 07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-212237 A | 8/2001 |
| JP | 2002-500933 T | 1/2002 |
| JP | 2002-502296 T | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-532500 T | 11/2003 |
| JP | 2003-533288 A | 11/2003 |
| JP | 2004-533282 T | 11/2004 |
| JP | 2004-537376 A | 12/2004 |
| JP | 2005-508214 A | 3/2005 |
| JP | 2005-177503 A | 7/2005 |
| JP | 2004-33737 A | 8/2005 |
| JP | 2006-223858 A | 8/2006 |
| JP | 2007-207611 A | 8/2007 |
| JP | 2008-284177 A | 11/2008 |
| NZ | 335985 A | 4/2001 |
| NZ | 573171 A | 11/2010 |
| NZ | 573350 A | 12/2010 |
| WO | WO 87/07843 A1 | 12/1987 |
| WO | WO 88/08725 | 11/1988 |
| WO | WO 88/10129 A1 | 12/1988 |
| WO | WO 98/10129 A1 | 12/1988 |
| WO | WO 92/19296 A | 11/1992 |
| WO | WO 93/02186 A1 | 2/1993 |
| WO | WO 93/21986 A2 | 11/1993 |
| WO | WO 93/23098 A1 | 11/1993 |
| WO | WO 94/04207 A1 | 3/1994 |
| WO | WO 94/07554 A1 | 4/1994 |
| WO | WO 94/11041 | 5/1994 |

(56) References Cited

FOREIGN PATENT DOCUMENTS

| | | |
|---|---|---|
| WO | WO 94/13342 A1 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/29720 A1 | 11/1995 |
| WO | WO 95/31235 A1 | 11/1995 |
| WO | WO 95/35126 A1 | 12/1995 |
| WO | WO 96/30065 A1 | 10/1996 |
| WO | WO 97/10865 A1 | 3/1997 |
| WO | WO 97/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 99/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 | 6/2000 |
| WO | WO 00/50107 A1 | 8/2000 |
| WO | WO 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/77384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | WO 02/074361 A2 | 9/2002 |
| WO | WO 03/013632 A2 | 2/2003 |
| WO | WO 03/015846 A2 | 2/2003 |
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 | 11/2003 |
| WO | WO 03/097133 | 11/2003 |
| WO | WO 03/099358 A2 | 12/2003 |
| WO | WO 2004/007554 A1 | 1/2004 |
| WO | WO 2004/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 A1 | 10/2004 |
| WO | WO 2004/101025 A2 | 11/2004 |
| WO | WO 2004/108194 A1 | 12/2004 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | WO 2005/058393 A2 | 6/2005 |
| WO | WO 2005/058396 A1 | 6/2005 |
| WO | WO 2005/070481 A1 | 8/2005 |
| WO | WO 2005/082438 A3 | 9/2005 |
| WO | WO 2005/097238 A1 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | WO 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/066152 A2 | 6/2007 |
| WO | WO 2007/122193 A1 | 11/2007 |
| WO | WO 2007/129324 A2 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 2010/023303 A1 | 3/2010 |
| WO | WO 2012/000835 A1 | 1/2012 |

OTHER PUBLICATIONS

International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 200608164-0.
International Search Report dated Sep. 5, 2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
Australian Search Report dated Dec. 11, 2007; Application No. 200608165-7.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.

(56) References Cited

OTHER PUBLICATIONS

International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/1132006/002792.
European Search Report dated Feb. 1, 2006; Application No. 05255298.1.
Great Britain Search Report dated Sep. 22, 2006; Application No. GB0610860.9.
International Search Report dated Aug. 22, 2007; International Application No. PCT/GB2007/001992.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.
European Search Report dated Aug. 3, 2011; Application No. 11170040.
European Search Report dated Aug. 3, 2011; Application No. 11163779.9.
Singapore Search Report dated Mar. 15, 2012; Application No. SG 201007017-5.
European Search Report dated Jul. 20, 2011; Application No. 11163762.5.
Australian Search Report dated Feb. 26, 2008; Application No. SG 200608071-7.
International Search Report dated Sep. 5, 2005; International Application No. PCT/GB2005/002137.
European Search Report dated Feb. 28, 2011; Application No. 10179733.0.
European Search Report dated Mar. 4, 2011; Application No. 10179736.3.
European Search Report dated Apr. 28, 2015; Application No. 15153304.9.
European Search Report dated Jun. 16, 2011; Application No. 11160134.0.
European Search Report dated Apr. 17, 2012; International Application No. 12157660.7.
European Search Report dated Apr. 17, 2012; International Application No. 12157661.5.
European Search Report Dated Oct. 16, 2012; International Application No. 12177505.0.
European Search Report dated Aug. 4, 2011; Application No. 11169691.0.
Great Britain Search Report dated Sep. 29, 2006; Application No. GB0610856.7.
Great Britain Search Report dated Sep. 19, 2006; Application No. GB0610861.7.
European Search Report dated Oct. 15, 2013; Application No. 12182553.3.
Great Britain Search Report dated Dec. 9, 2013; Application No. GB1310394.0.
International Search Report dated Sep. 8, 2014; International Application No. PCT/EP2014/062163.
Great Britain Search Report dated Dec. 8, 2013; Application No. GB1310389.0.
International Search Report dated Sep. 8, 2014; International Application No. PCT/EP2014/062166.
Great Britain Search Report dated Dec. 9, 2013; Application No. GB1310402.1.
International Search Report dated Sep. 17, 2014; International Application No. PCT/EP2014/062167.
International Search Report dated Jan. 29, 2015; International Application No. PCT/EP2014/062167.
Great Britain Search Report dated Dec. 9, 2013; Application No. GB1310392.4.
International Search Report dated Sep. 9, 2014; International Application No. PCT/EP2014/062168.
Great Britain Search Report dated Dec. 10, 2013; Application No. GB1310393.2.
International Search Report dated Sep. 8, 2014; International Application No. PCT/EP2014/062162.
Great Britain Search Report dated Dec. 10, 2013; Application No. GB1310372.6.
International Search Report dated Sep. 16, 2014; International Application No. PCT/EP2014/062160.
International Preliminary Report dated Dec. 15, 2015; International Application No. PCT/EP2014/062163.

(56) References Cited

OTHER PUBLICATIONS

International Preliminary Report dated Dec. 15, 2015; International Application No. PCT/EP2014/062166.

\* cited by examiner

INJECTION DEVICE

FIELD OF THE INVENTION

The present invention relates to an injection device of the type that receives a syringe, extends it, discharges its contents and then retracts it automatically.

BACKGROUND OF THE INVENTION

Known injection devices are shown in WO 95/35126 and EP-A-0 516 473 and tend to employ a drive spring and some form of release mechanism that releases the syringe from the influence of the drive spring once its contents are supposed to have been discharged, to allow it to be retracted by a return spring.

Often, such injection devices are required to work with sealed hypodermic syringes which typically have a hermetically sealed cover or "boot" that covers the hypodermic needle and maintains the sterility of the syringe contents. Naturally, it is necessary to maintain the sterility of the syringe contents up to the point of administration, which means that for devices that are designed to be disposable, the boot must be removed with the syringe inside the injection device.

Generally, the action required to remove the boot from the syringe entails either pulling the boot away from the syringe or twisting the boot and, either at the same time or subsequently, pulling the boot away from the syringe.

Co-pending United Kingdom patent application no. 0412051.5, the contents of which is incorporated herein by reference, describes a cap for an injection device that connects to the boot of the syringe so that removal of the housing closure member from the housing causes removal of the boot from the syringe.

In certain types of syringe, for example a Bünder ReadyJect™ type syringe, the boot must be twisted to break a frangible joint before it can be pulled off. Since the syringe is contained in the housing and not held directly by a user, it must be supported rigidly in the housing so that rotation of the boot does not cause rotation of the syringe which would result in the boot not being removed. This is particularly the case when significant rotational force is required to remove the boot and/or break the frangible joint.

The cylindrical shape of a syringe does not lend itself to being supported against rotation, especially since the syringes which are used with injection devices of the type described herein are often made of glass which can fracture.

SUMMARY OF THE INVENTION

The injection devices of the present invention are designed to deal with the aforementioned problems.

In view of the foregoing and in accordance with the present invention, there is provided an injection device comprising:
- a housing comprising a syringe having a discharge nozzle which is movable between a retracted position in which the discharge nozzle is contained within the housing and an extended position in which the discharge nozzle extends from the housing;
- a syringe cap for enclosing the discharge nozzle and removable from the syringe by rotation relative to the syringe; and
- a syringe carrier adapted to restrain rotation of the syringe relative to the housing as the cap is removed.

Thus, the syringe cap can be removed easily by rotating it with the syringe held firmly in the housing.

In one embodiment of the present invention, the syringe carrier comprises a grip adapted to restrain rotation of the syringe relative to the housing.

Preferably, the grip comprises at least one deformable rib. Thus, a firm connection is formed between the syringe and the syringe carrier on insertion of the syringe into the syringe carrier.

Preferably, the syringe carrier comprises a ring through which the discharge nozzle of the syringe extends, the ring including the grip on its inner circumference.

In one embodiment of the present invention, the syringe comprises a syringe body and at least one spline protruding radially from the syringe body extending at least in part along the length of the body of the syringe.

The grip may comprise at least one rib engageable with the at least one spline on the syringe body. This way, the rib and spline may interlock with each other in a tooth-like way to form improved resistance to rotation.

At least one spline may be located adjacent the discharge nozzle.

A housing cap may be releasably attached over an aperture of the housing through which the discharge nozzle extends in use, wherein the housing cap is in communication with the syringe cap.

BRIEF DESCRIPTION OF THE DRAWINGS

The invention will now be described by way of example with reference to the accompanying drawings, in which.

DETAILED DESCRIPTION OF THE DRAWINGS

Figure 1:
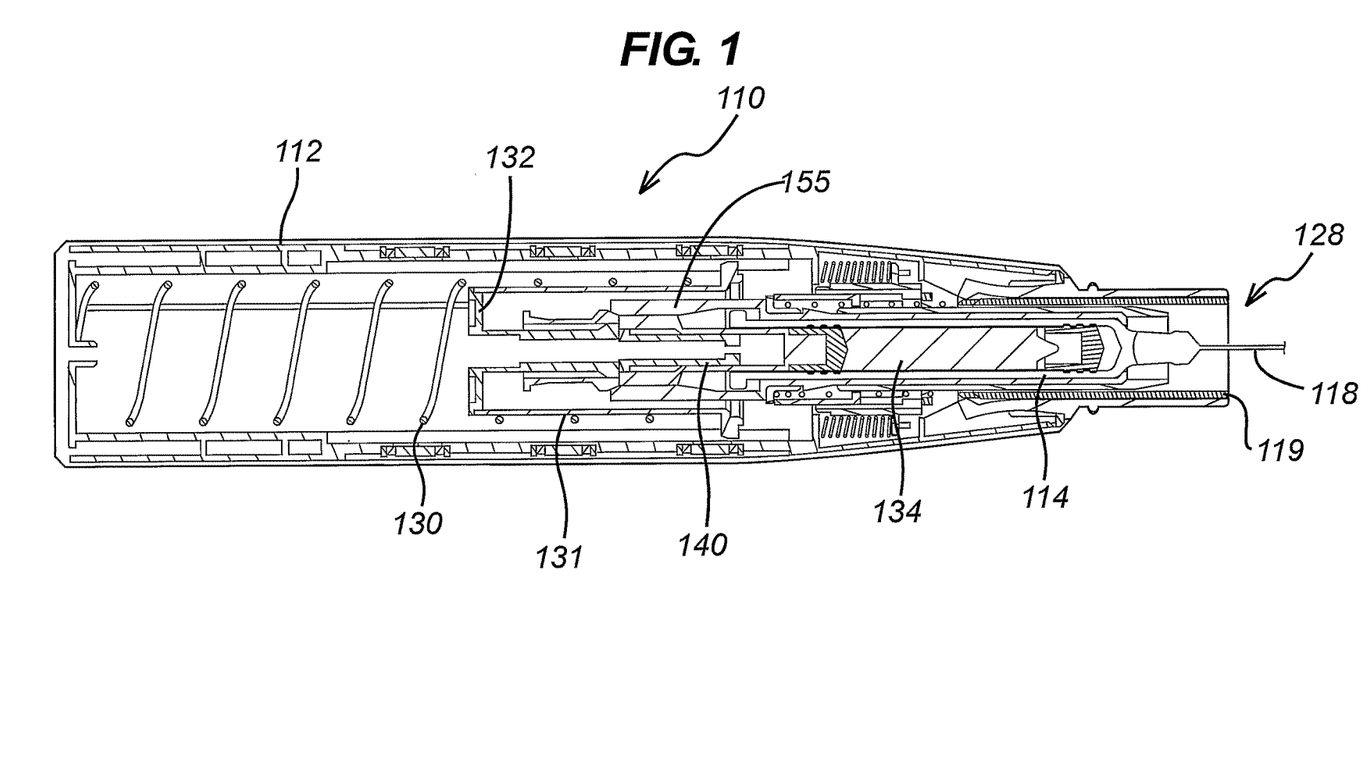
FIG. 1 shows a cross-sectional view of an injection device according to the present invention.
Figure 2:
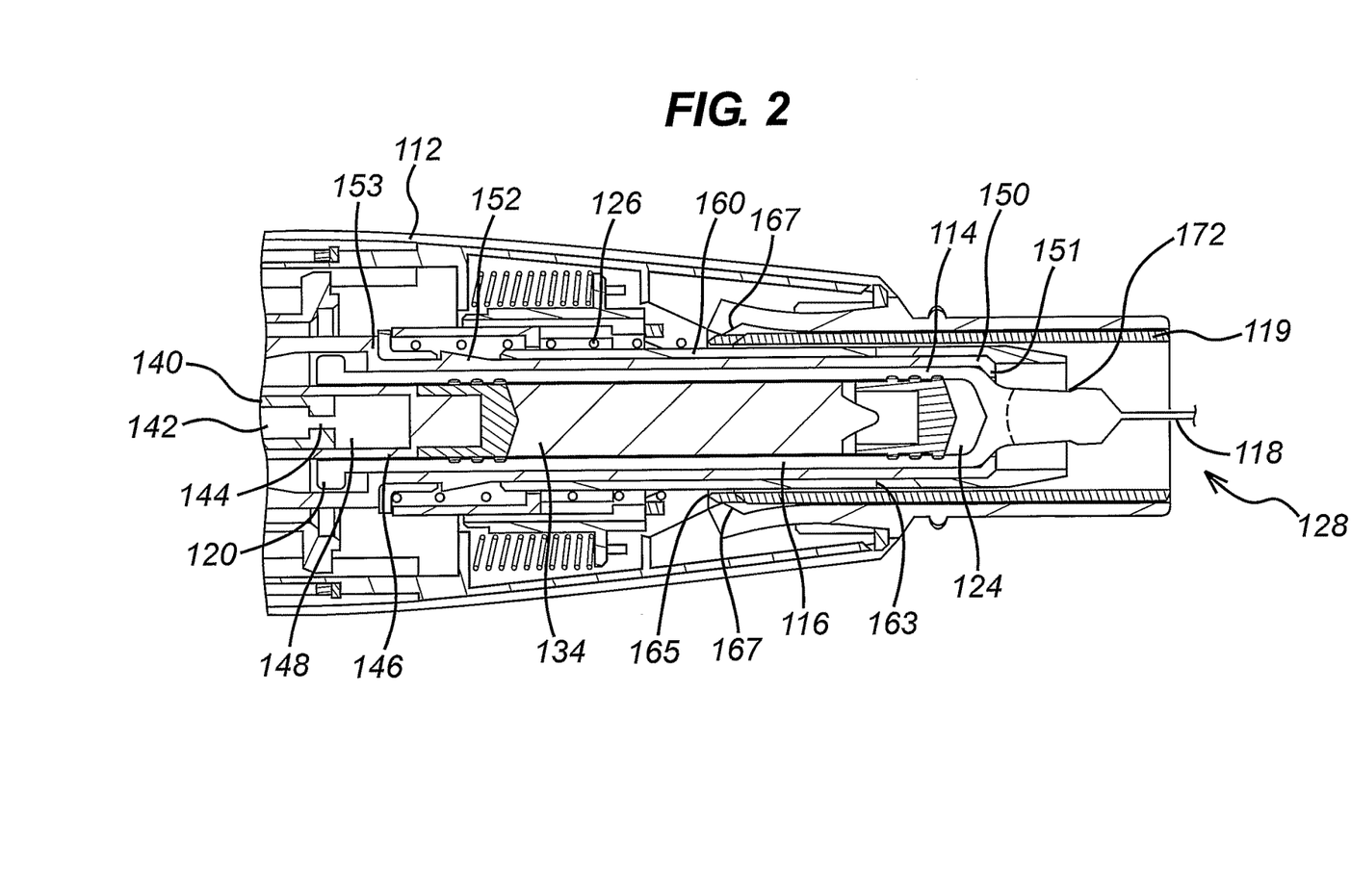
FIG. 2 shows an enlarged part of the injection device shown in FIG. 1.

FIGS. 1 and 2 show an injection device 110, having an injection device housing 112. The end of the housing 112 has an exit aperture 128, through which the end of a sleeve 119 can emerge.

The housing 112 contains a hypodermic syringe 114 of conventional type, including a syringe body 116 defining a reservoir and terminating at one end in a hypodermic needle 118 and at the other in a flange 120. The syringe body 116 is of substantially constant diameter along the length of the reservoir, and is of significantly smaller diameter close to the end of the syringe which terminates in the hypodermic needle. A drive element 134 acts through the bung of the syringe to discharge the contents of the syringe 114 through the needle 118. This drive element 134 constrains a drug 124 to be administered within the reservoir defined by syringe body 116. Whilst the syringe illustrated is of hypodermic type, this need not necessarily be so. Transcutaneous or ballistic dermal and subcutaneous syringes may also be used with the injection device of the present invention.

Figures 3, 4:
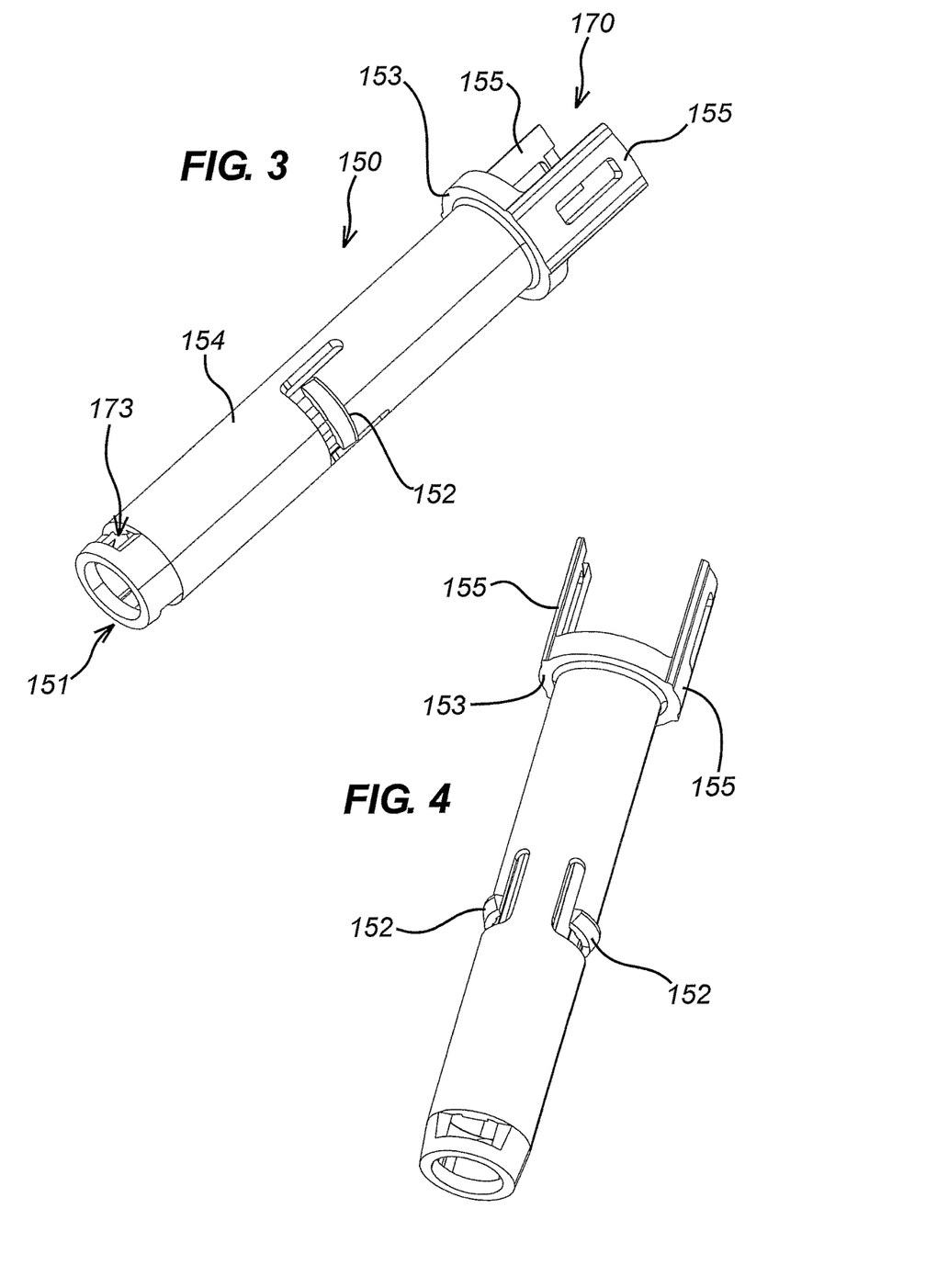
FIG. 3 shows a perspective view of a syringe carrier for use in the present invention from a first direction.
FIG. 4 shows a perspective view of the syringe carrier of FIG. 3 from a second direction.

As illustrated, the syringe is housed within a syringe carrier 150. The syringe carrier is best seen in FIGS. 3 and 4. The syringe carrier 150 has a proximal end 151 through which the needle 118 of the syringe protrudes. The needle 118 is attached to the syringe body 116 of the syringe by a needle sub-assembly 172 which has a reduced diameter. At the proximal end 151 of the syringe carrier 150, there is a section of reduced diameter 173 which supports the end of the syringe 114 on its body 116. The syringe carrier 150 also includes a pair of flexible projections 152. The pair of flexible projections 152 communicate with a corresponding pair of locking apertures on a return spring support 160 so that the syringe carrier 150 cannot move relative to the return spring support 160. The syringe carrier 150 also comprises a bearing surface 153 close to its second end, against which a corresponding bearing surface of the return spring support 160 is biased by a return spring 126. The return spring 126, via the return spring support 160 and the syringe carrier 150 biases the syringe 114 from an extended position in which the needle 118 extends from the aperture 128 in the housing 112 to a retracted position in which the needle 118 is contained within the housing 112.

The syringe carrier 150 comprises a sheath 154 into which the syringe 114 can be inserted from a distal end 170. The syringe 114 is provided with a boot (not shown). If the syringe were to fail or break, the sheath 154, which surrounds the syringe 114 along its length, would contain the broken pieces of syringe and reduce the likelihood of them from escaping from the injection device 110.

The housing is further provided with a resilient latch member 161 that is biased into a position in which it engages a locking surface 163 on the return spring support 160. Before engaging the locking surface 163, the latch member 161 also extends through a latch opening 165 in the sleeve 119. The latch member 161 includes a ramped surface 167 against which an edge of the latch opening 165 acts in the manner of a cam acting on a cam follower.

The housing also includes an actuator, and a drive which here takes the form of a compression drive spring 130. Drive from the drive spring 130 is transmitted via a multi-component drive to the piston of the syringe 114 to advance the syringe from its retracted position to its extended position and discharge its contents through the needle 118. The drive accomplishes this task by acting directly on the drug 124 and the syringe 114. Static friction between the drive element 134 and the syringe body 116 initially ensures that they advance together, until the return spring 126 bottoms out or the syringe body 116 meets some other obstruction (not shown) that retards its motion.

The multi-component drive between the drive spring 130 and the syringe 114 consists of three principal components. A drive sleeve 131 takes drive from the drive spring 130 and transmits it to a first drive element 132. This in turn transmits drive to the drive element 134 already mentioned.

The drive element 132 includes a hollow stem 140, the inner cavity of which forms a collection chamber 142 in communication with a vent 144 that extends from the collection chamber through the end of the stem 140. The second drive element 134 includes a blind bore 146 that is open at one end to receive the stem 140 and closed at the other. As can be seen, the bore 146 and the stem 140 define a fluid reservoir 148, within which a damping fluid is contained.

A trigger (not shown) is provided on the housing 112 remote from the exit aperture 128. The trigger, when operated, serves to decouple the drive sleeve 131 from the housing 112, allowing it to move relative to the housing 112 under the influence of the drive spring 130. The operation of the device is then as follows.

Initially, the return spring carrier 152, and consequently the syringe carrier 150 and syringe 114, are prevented from movement by the resilient latch member 161. By moving the sleeve 119 in a direction into the housing 112, the edge of the latch opening 165 is brought into contact with the ramped surface 167 of the latch member 161, causing the latch member 161 to move outwards and thus to disengage from the return spring support 160. Once the latch member 161 has disengaged from the locking surface 163, the syringe is free to move.

The actuator is then depressed and the drive spring 130 is released. The drive spring 130 moves the drive sleeve 131, the drive sleeve 131 moves the first drive element 132 and the first drive element 132 moves the second drive element 134. The second drive element 134 moves and, by virtue of static friction and hydrostatic forces acting through the drug 124 to be administered, moves the syringe body 114 against the action of the return spring 126.

The syringe body 114 moves the syringe carrier 150, which in turn moves the return spring support 160 and compresses the return spring 126. The hypodermic needle 118 emerges from the exit aperture 128 of the housing 112. This continues until the return spring 126 bottoms out or the syringe body 116 meets some other obstruction (not shown) that retards its motion. Because the static friction between the second drive element 134 and the syringe body 116 and the hydrostatic forces acting through the drug 124 to be administered are not sufficient to resist the full drive force developed by the drive spring 130, at this point the second drive element 134 begins to move within the syringe body 116 and the drug 124 begins to be discharged. Dynamic friction between the second drive element 134 and the syringe body 116 and hydrostatic and hydrodynamic forces now acting through the drug 124 to be administered are, however, sufficient to retain the return spring 126 in its compressed state, so the hypodermic needle 118 remains extended.

Before the second drive element 134 reaches the end of its travel within the syringe body 116, so before the contents of the syringe have fully discharged, flexible latch arms linking the first and second drive elements 132, 134 reach a constriction within the housing 112 formed by arms 155 at the end of the syringe carrier which is nearest to the flange 120 of the syringe 114. The constriction moves the flexible latch arms to a position so that they no longer couple the first drive element 132 to the second drive element 134. Once this happens, the first drive element 132 acts no longer on the second drive element 134, allowing the first drive element 132 to move relative to the second drive element 134.

Because the damping fluid is contained within a reservoir 148 defined between the end of the first drive element 132 and the blind bore 146 in the second drive element 134, the volume of the reservoir 146 will tend to decrease as the first drive element 132 moves relative to the second drive element 134 when the former is acted upon by the drive spring 130. As the reservoir 148 collapses, damping fluid is forced through the vent 144 into the collection chamber 142. Thus, once the flexible latch arms have been released, some of the force exerted by the drive spring 130 does work on the damping fluid, causing it to flow though the constriction formed by the vent 144; the remainder acts hydrostatically through the fluid and through friction between the first and second drive elements 132, 134, thence via the second drive element 134. Consequently, the second drive element 134 continues to move within the syringe body 116 and the drug 124 continues to be discharged. Losses associated with the flow of the damping fluid do not attenuate the force acting on the body of the syringe to a great extent. Thus, the return spring 126 remains compressed and the hypodermic needle remains extended.

After a time, the second drive element 134 completes its travel within the syringe body 116 and can go no further. At this point, the contents of the syringe 114 are completely discharged and the force exerted by the drive spring 130 acts to retain the second drive element 134 in its terminal position and to continue to cause the damping fluid to flow though the vent 144, allowing the first drive element 132 to continue its movement.

Before the reservoir 148 of fluid is exhausted, flexible latch arms linking the drive sleeve 131 with the first drive element 132 reach another constriction within the housing 112. The constriction moves the flexible latch arms so that they no longer couple the drive sleeve 131 to the first drive element 132. Once this happens, the drive sleeve 131 acts no longer on the first drive element 132, allowing them to move relative each other. At this point, the forces developed by the drive spring 130 are no longer being transmitted to the syringe 114. The only force acting on the syringe will be the return force from the return spring 126 which acts on the end of the syringe 114 nearest to the needle 118 via the return spring support 160 and the syringe carrier 150. Consequently, the syringe is returned to its retracted position and the injection cycle is complete.

Figure 5:
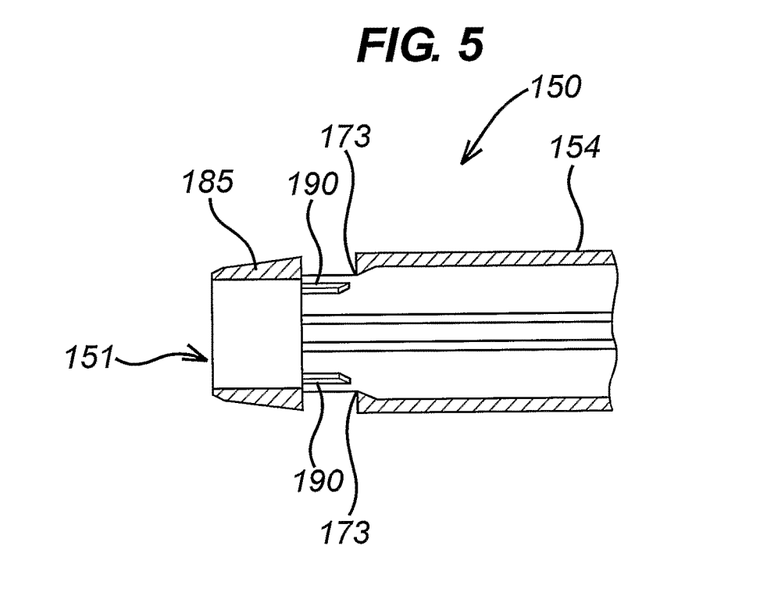
FIG. 5 shows an enlarged cross-sectional view of the end of the syringe carrier of FIGS. 3 and 4.
Figure 6:
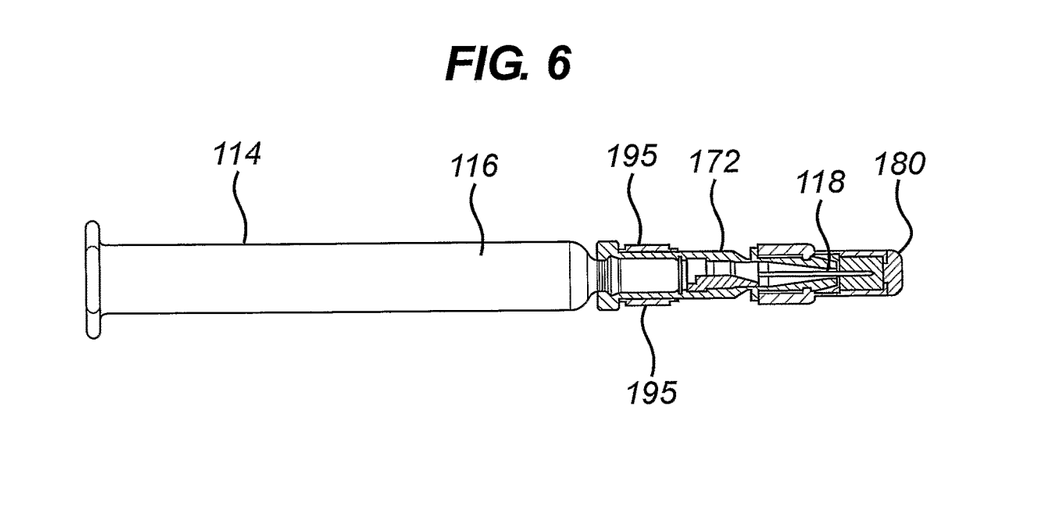
FIG. 6 shows a cross-sectional view of a syringe for use in the present invention.

FIG. 5 shows an enlarged cross-sectional view of the proximal end 151 of the syringe carrier 150 and FIG. 6 shows, in isolation, the syringe 116 with syringe cap 180 over the discharge needle 118. The section 173 of reduced cross sectional area in the syringe carrier 150 can be seen in greater detail in FIG. 5. Also provided at the proximal end 151 is a ring 185 through which the syringe cap 180 and needle sub-assembly 172 protrude when the syringe 114 is inserted into the syringe carrier 150. On the inner circumference of the ring 185, there is provided a plurality of deformable ribs 190 which deform resiliently to provide a grip on the needle-sub-assembly 172 when the syringe 114 is inserted into the syringe carrier 150. The grip provided by the deformable ribs 190 prevents rotation of the syringe 114 within the syringe carrier 150.

On the outer surface of the needle sub-assembly 195 of the syringe 114, there is a plurality splines 195 which protrude radially from the syringe body and extend along their length, at least in part, along the length of the needle sub-assembly 195 of the syringe 114.

In one embodiment of the invention, the splines 195 and ribs 190 may be arranged to engage each other as interlocking teeth, thereby providing improved grip and resistance to rotation.

Figure 7:
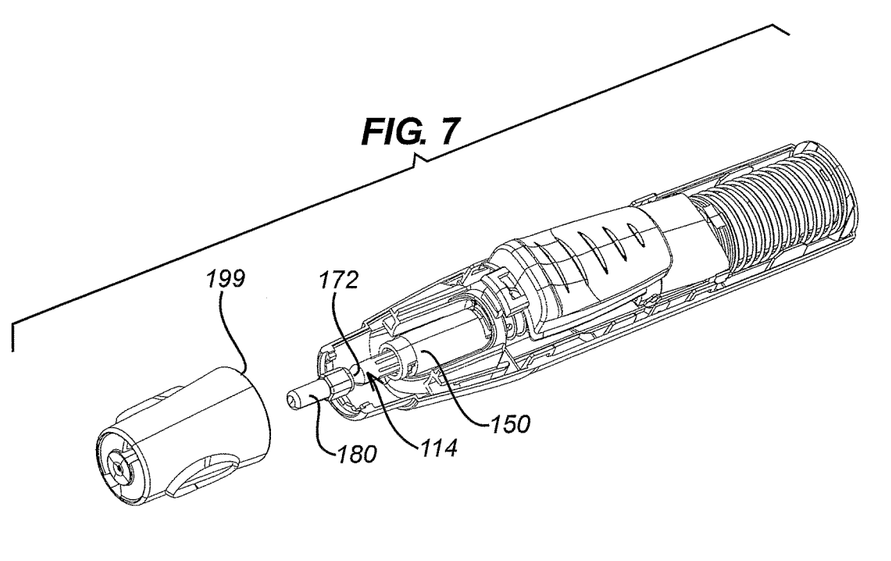
FIG. 7 shows a perspective view of the injection device of the present invention.

FIG. 7 shows the injection device with a housing cap 199 into which the syringe cap 180 is inserted on manufacture of the injection device 110. The syringe cap 180 is held rigidly in the housing cap 199 so that, on rotation of the housing cap 199, the syringe cap 180 is also rotated (whilst the syringe 114 is gripped against the rotation in the syringe carrier 150), thereby breaking a frangible connection of the syringe cap 180 to the needle sub-assembly 172.

It will of course be understood that the present invention has been described above purely by way of example and modifications of detail can be made within the scope of the invention.

The invention claimed is:

1. An injection device comprising:
   a housing comprising a conventional syringe having a syringe body defining a reservoir and terminating at one end in a discharge nozzle, the syringe being movable relative to the housing between a retracted position in which the discharge nozzle is contained within the housing and an extended position in which the discharge nozzle extends from the housing;
   a housing cap secured to a syringe cap, said syringe cap enclosed within said housing cap and for enclosing the discharge nozzle, said housing cap removable from the syringe and the syringe cap removable from the discharge nozzle by rotation of said housing cap relative to the syringe; and
   a syringe carrier adapted to restrain rotation of the syringe relative to the housing as the housing cap and syringe cap are removed, the syringe carrier comprising a sheath surrounding the syringe along its length;
   wherein the syringe carrier comprises a grip at its proximal end adapted to restrain rotation of the syringe relative to the syringe carrier.

2. The injection device of claim 1, wherein the grip comprises at least one deformable rib.

3. The injection device of claim 1 or claim 2, wherein the syringe carrier comprises a ring through which the discharge nozzle of the syringe extends, the ring including the grip on its inner circumference.

4. The injection device of claim 1, further comprising at least one spline protruding radially from the syringe body extending at least in part along a length of the syringe body.

5. The injection device of claim 4, wherein the grip comprises at least one rib engageable with the at least one spline on the syringe body.

6. The injection device of claim 4, wherein the at least one spline is located adjacent the discharge nozzle.

\* \* \* \* \*